United States Patent [19]

Hayhurst et al.

[11] Patent Number: 5,236,445
[45] Date of Patent: Aug. 17, 1993

[54] EXPANDABLE BONE ANCHOR AND METHOD OF ANCHORING A SUTURE TO A BONE

[75] Inventors: John O. Hayhurst, Milwaukie, Oreg.; Alan A. Small, Needham; Jeffrey C. Cerier, Franklin, both of Mass.

[73] Assignee: American Cyanamid Company, Stamford, Conn.

[21] Appl. No.: 882,723

[22] Filed: May 14, 1992

Related U.S. Application Data

[63] Continuation-in-part of Ser. No. 681,070, Apr. 5, 1991, which is a continuation-in-part of Ser. No. 547,787, Jul. 2, 1990, Pat. No. 5,037,422.

[51] Int. Cl.⁵ ............................................. A61B 17/00
[52] U.S. Cl. ..................... 606/232; 606/73; 606/75; 411/511
[58] Field of Search ............. 606/232, 220, 236, 204, 606/73, 170, 134, 73–75; 411/511

[56] References Cited

U.S. PATENT DOCUMENTS

| 3,845,772 | 11/1974 | Smith | 128/335 |
|---|---|---|---|
| 4,275,717 | 6/1981 | Bolesky | 128/92 |
| 4,409,974 | 10/1983 | Freedland | 128/92 |
| 4,454,875 | 6/1984 | Pratt et al. | 128/92 |
| 4,476,861 | 10/1984 | Dimakos et al. | 128/303 |
| 4,532,926 | 8/1985 | O'Holla | 128/334 |
| 4,632,100 | 12/1986 | Somers et al. | 606/73 |
| 4,653,486 | 3/1987 | Coker | 128/92 |
| 4,772,286 | 9/1988 | Goble et al. | 623/13 |
| 4,776,328 | 10/1988 | Frey et al. | 128/92 |
| 4,946,468 | 8/1990 | Li | 606/232 |
| 5,100,417 | 3/1992 | Cerier et al. | 606/139 |

FOREIGN PATENT DOCUMENTS

| 0260970 | 3/1988 | European Pat. Off. |
| 2606270 | 5/1988 | France |
| WO/8910096 | 11/1989 | PCT Int'l Appl. |

OTHER PUBLICATIONS

Russell Warren, M.D., Technique for Using the TAG Tissue Anchor–Rod Style, Published Jul. 16, 1990.
John O. Hayhurst, M.D., Technique for Using the TAG Tissue Anchor–Wedge Style, Published Jul. 16, 1990.
Arthrex Brochure—"Arthrex ESP System: Expanding Suture Plug", Feb. 1991, [Published prior to Mar. 1, 1991].

*Primary Examiner*—Stephen C. Pellegrino
*Assistant Examiner*—Gary Jackson
*Attorney, Agent, or Firm*—Douglas E. Denninger

[57] ABSTRACT

A bone anchor, for securing a suture to a bone, has an open proximal end and a body that tapers to a solid distal tip. The anchor is placed deep in a borehole in a bone using an insertion instrument that is inserted through the open proximal end of the anchor. The tip of the instrument is a spherical knob that snaps into a corresponding recess inside the anchor. The instrument has an oval cross-section that does not bear against the walls of the anchor during insertion. Once the anchor is in place, however, the anchor is expanded by rotating the instrument to bring the exterior of the instrument into contact with the walls of the anchor. The anchor is free to pivot about the spherical knob on the instrument, which allows the anchor to orient itself to the shape and size of the borehole.

24 Claims, 2 Drawing Sheets

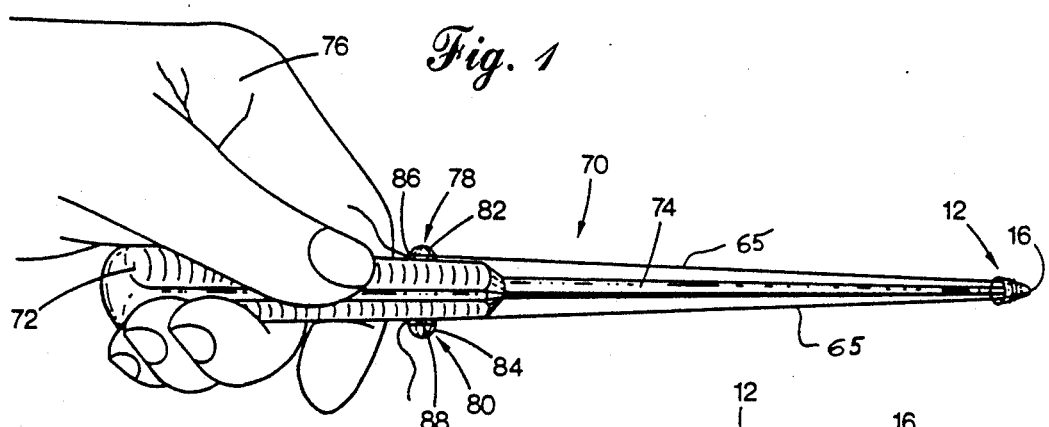
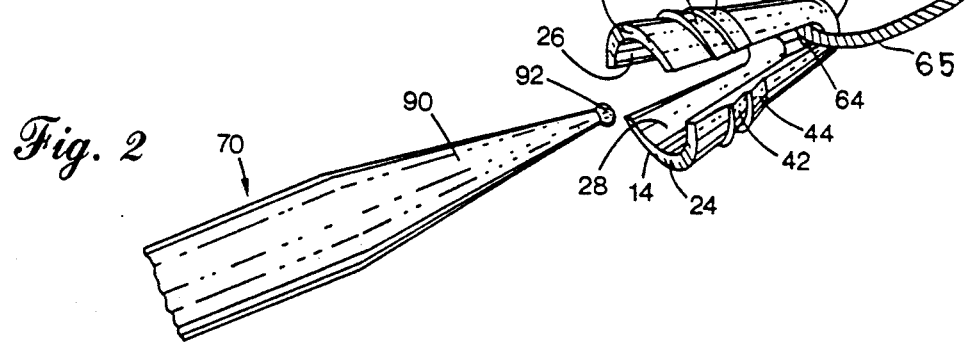
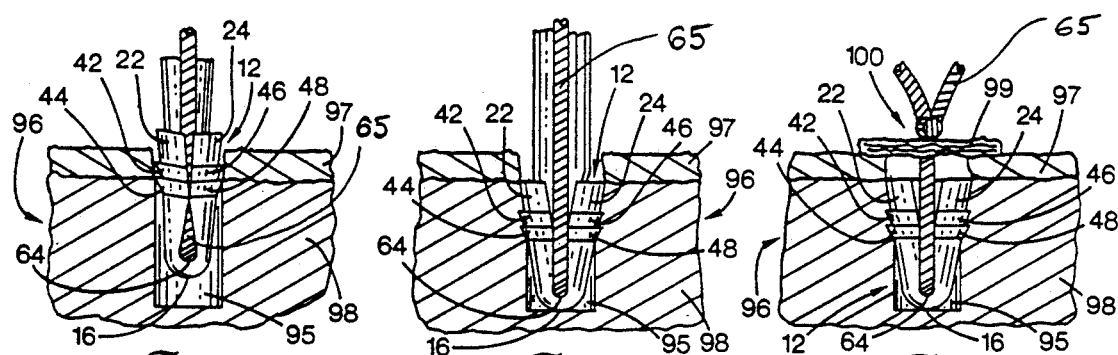
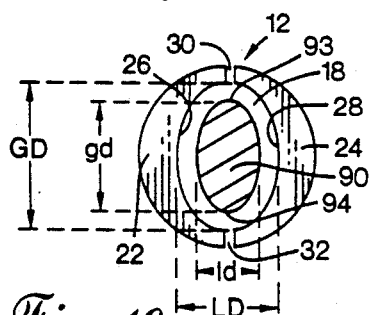
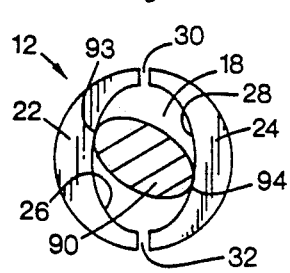
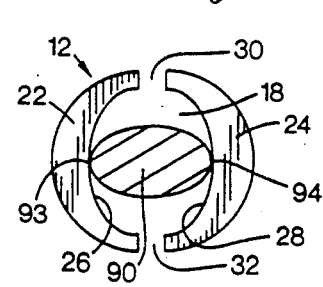

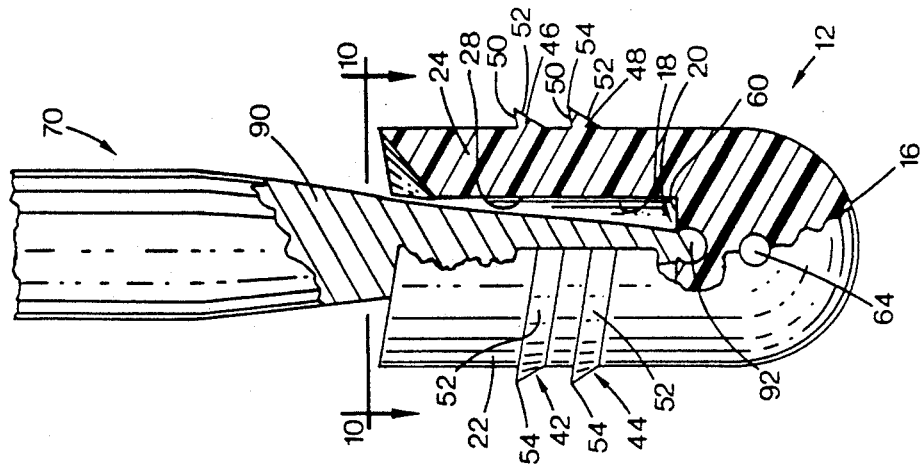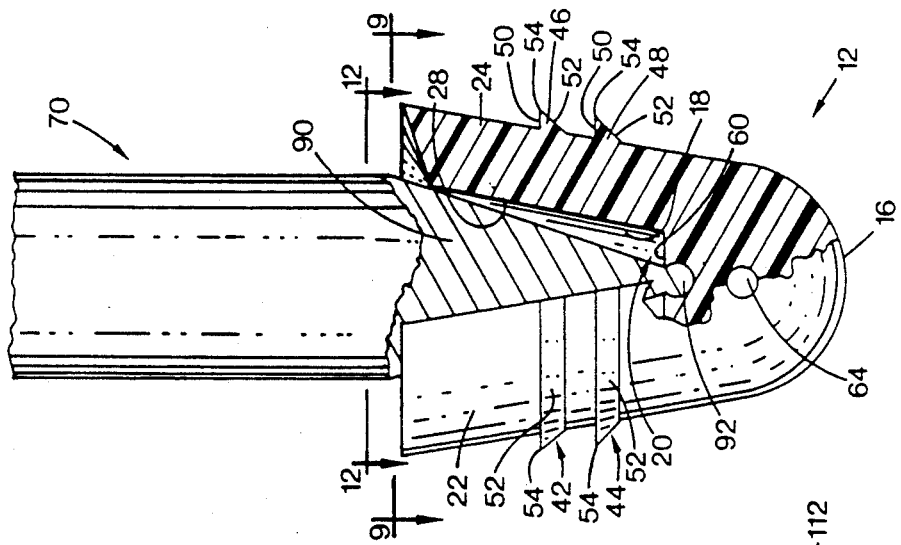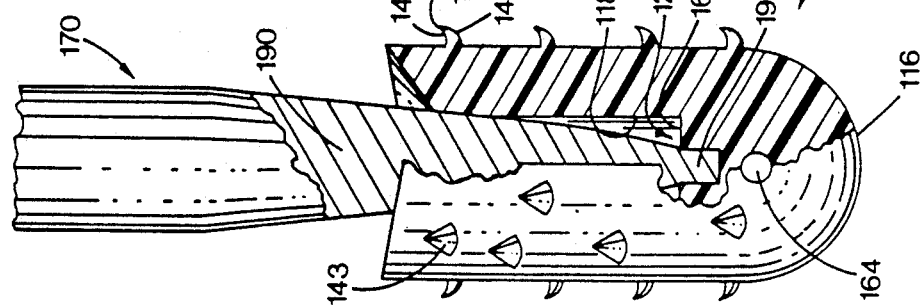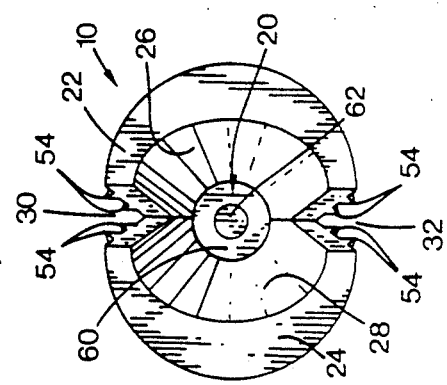

EXPANDABLE BONE ANCHOR AND METHOD OF ANCHORING A SUTURE TO A BONE

BACKGROUND INFORMATION

This application is a continuation-in-part of U.S. patent application Ser. No. 07/681,070, filed Apr. 5 1991, herein incorporated by reference, which is a continuation-in-part of U.S. application Ser. No. 07/547,787, filed Jul. 2, 1990, now U.S. Pat. No. 5,037,422.

FIELD OF THE INVENTION

This invention relates to anchors for surgical sutures, and more particularly relates to bone anchors that are inserted into a hole formed in a bone by a drilling operation.

GENERAL DISCUSSION OF BACKGROUND

Suture anchors are used to secure sutures within openings formed in bones during joint reconstructive surgery and arthroscopic surgical procedures. The anchor is typically placed in a bone and connected to a suture that could otherwise not be secured to dense osseous material. Such suture anchors are used, for example, to anchor ligaments or tendons to bones in knee, shoulder and elbow reconstruction and repair operations. Important attributes of bone anchors are that they be easy to insert, and provide a firm anchor. Unintended dislodgement of the anchor after surgery can have serious adverse consequences, hence much importance is placed on the ability of an anchor to resist extraction or withdrawal forces exerted by the attached suture. Such bone anchors may be bioabsorbable or non-bioabsorbable, depending on the type of operation and preference of the surgeon.

An early type of bone anchor took the form of a barb shaped like a fish hook that was inserted into a borehole and hooked into the soft marrow of the bone. A later approach to suture anchors is disclosed in U.S. Pat. No. 4,738,255, which discloses a suture anchor delivery tool that manipulates a specialized two-piece anchor system. The anchor includes a collar with a slotted distal end that expands when a ram member is pulled into the distal end of the collar. The ram is pulled into the slotted collar by tension exerted on a line that runs axially through a mandrel from which the collar is suspended. This complex arrangement requires a specialized anchor delivery system for manipulating the ram and slotted ring. The expanded bone anchor it produced also tapers proximally such that extraction forces exerted on the anchor tend to collapse the enlarged distal portion of the anchor.

U.S. Pat. No. 4,013,071 discloses an orthopedic screw having an expandable tip that enhances bone retention. The expandable tip includes side slits that extend through the distal end of the screw. The side slits produce a distal screw tip that is flared by axially advancing a rod-shaped expansion member through an internal bore of the orthopedic screw. The distal expansion of the screw persists only as long as the rod shaped expansion member is present. Once the expansion member is withdrawn, the tip returns to its original collapsed shape.

Yet another implantable bone anchor is shown in U.S. Pat. No. 4,409,974 wherein a frustoconical anchor body is retained in a bore hole by a plurality of arms that pivot radially outwardly in the bore. The arms are expanded by exerting tension on a series of threads that run axially through an insertion tube. U.S. Pat. No. 4,454,875 discloses an osteal staple having barbed legs with a triangular cross-section that resist withdrawal of the staple from bone.

The bone anchors shown in these prior patents require multiple parts that increase surgical risk and expense. Multiplication of parts increases the possibility that one of the parts will be dislodged or dropped during surgical placement, or lost internally in a patient. These prior anchor systems are also complex and time-consuming to use, requiring assembly and manipulation of multiple parts. Such time-consuming assembly of devices can be expensive to use because of the high cost of time in surgical suites Finally, many of these prior expandable bone anchors can be collapsed by the tension exerted on them by the sutures they anchor.

It is accordingly a primary object of the present invention to provide an improved bone anchor that is inexpensive to manufacture and simple to install Another object of the invention is to provide an improved bone anchor that does not require time-consuming and expensive assembly of multiple parts, or complex remote manipulation to expand the anchor Yet another object of the invention is to provide an improved bone anchor having a minimal number of parts that reduces the likelihood of inadvertent loss of anchor pieces during placement.

Yet another object of the invention is to provide an improved bone anchor that better resists extraction forces exerted by suture tension.

Still another aspect of the present invention is to provide an improved bone anchor that is compact and self-seating.

Another important object of the invention is to provide an improved bone anchor that may be formed by a simple molding operation with no close tolerance assembly operations required.

These and other objects of the invention will be understood more clearly by reference to the following detailed description and drawings.

SUMMARY OF THE INVENTION

The foregoing objects are achieved by a bone anchor having an elongated body with a distal tip and an open expandable proximal end. The body defines an expansion chamber that communicates proximally with the open end of the anchor such that an expansion instrument can be inserted directly into the chamber through the open proximal end and rotated to expand the anchor. A distal end of the chamber forms a seat against which an expansion instrument may rest while it rotates in the expansion chamber without axially advancing. In preferred embodiments, the seat is a cylindrical or spherical recess that is adapted to receive a correspondingly shaped tip of a rod-like expansion instrument. The spherical recess and instrument tip are especially preferred because they snap fit together and enhance freedom of movement between the anchor and instrument. Such freedom of movement helps the anchor seat itself in a bone hole.

An expansion slot extends longitudinally through the open proximal end of the body and allows the proximal portion of the body to expand in response to outwardly directed force applied to the body from within the expansion chamber. The expansion chamber preferably has a non-circular cross-section with at least one arcuate surface for engaging the rotary expansion tool as the tool rotates through a portion of a revolution. The tool is also non-circular in cross-section, and preferably has a cross-sectional shape that corresponds to the shape of the expansion chamber. In preferred embodiments the expansion chamber and tool both have an oval cross-section, but the greatest diameter of the tool is less than the greatest diameter of the chamber. The dimensions of the tool are preferably small enough that the tool can be inserted into the chamber without bearing against the chamber walls, and the tool can rotate through about at least forty-five degrees before the tool bears against the walls of the chamber. As the tool rotates beyond the point of first contacting the chamber wall, a rounded edge of the oval cross-section rod impinges against the arcuate face of the wall to begin spreading the proximal slitted portion of the body. As the rod is rotated through about ninety degrees from its initial orientation, the rounded edge of the rod bears against the arcuate wall to spread the anchor to the extent of the greatest diameter of the oval portion of the rod in the chamber.

The present invention also includes a method of anchoring a suture to a bone by first drilling a bore hole in the bone. The bone anchor is then inserted, distal end first, into the bore hole. An expansion instrument, such as a rod with an oblong or oval cross-section, is inserted into the expansion chamber through the open proximal end of the anchor. The slotted proximal end of the bone anchor is then expanded by rotating the instrument to bring the instrument into contact with the walls as the instrument rotates. The oblong or oval cross-section of the instrument permits it to rotate through at least a portion of a revolution before contacting the walls, such that the bone anchor is less likely to rotate with the instrument. In preferred embodiments, the distal tip of the instrument seats in a corresponding recess at the distal end of the expansion chamber. The recess provides a fixed pivot point about which the rod rotates to expand the anchor.

BRIEF DESCRIPTION OF THE DRAWINGS

FIG. 1 is a side elevational view of the bone anchor of the present invention secured to an instrument held by a surgeon for inserting the anchor into a bore hole and expanding the diameter of the anchor.

FIG. 2 is an enlarged, fragmentary perspective view of the bone anchor and instrument of the present invention, only the distal portion of the instrument being shown.

FIG. 3 is a cross-sectional, fragmentary view showing insertion of the bone anchor of the present invention into a pre-existing bore hole in bone.

FIG. 4 is a view similar to FIG. 3 showing the distal tip of the anchor seated against the bottom of a borehole, the anchor having been expanded as compared to FIG. 3.

FIG. 5 is a view similar to FIG. 4 showing the bone anchor securing soft tissue to the bone.

FIG. 6 is an enlarged, fragmentary view of the bone anchor and insertion tool shown in FIG. 3, portions of the bone anchor wall and instrument being broken away to reveal the structural relationship between the instrument and anchor before the anchor is expanded.

FIG. 7 is an enlarged, fragmentary view of the bone anchor as shown in FIG. 4 after the expansion instrument is rotated to expand the anchor.

FIG. 8 is a view, similar to FIG. 6, showing an alternative embodiment of the bone anchor and insertion tool.

FIG. 9 is a view taken along view lines 9—9 of FIG. 7, the expansion tool having been removed from the anchor.

FIG. 10 is a view taken along section lines 10—10 of FIG. 6, showing the relationship between the expansion tool and anchor before the anchor is expanded.

FIG. 11 is a view similar to FIG. 10, showing rotation of the expansion tool through about fifty degrees to bring the tool into initial contact with the walls of the anchor.

FIG. 12 is a view taken along lines 12—12 of FIG. 7, showing the relationship between the expansion tool and anchor after the tool has been rotated through about ninety degrees to expand the anchor body.

DETAILED DESCRIPTION OF PREFERRED EMBODIMENTS

The bone anchor of the present invention is best seen in FIGS. 1 and 2 to include an expandable, frustoconical anchor body 12 that is made of a resilient plastic material The width of body 12 tapers from an open proximal end 14 to a rounded, solid distal tip 16. Body 12 defines an internal expansion chamber 18 (FIGS. 10-12) that communicates proximally with open end 14 and distally with a guide seat 20 (FIGS. 6, 7 and 9) at the distal tip 16 of body 12. Expansion chamber 18 has an oblong ovoid cross-section defined by opposing, arcuate walls 22, 24 that provide a pair of opposing arcuate guide surfaces 26, 28.

A pair of opposing expansion slots 30, 32 (FIGS. 9-12) extend through walls 22, 24 along a portion of the length of body 12. Slots 30, 32 extend through proximal end 14 to separate completely the proximal aspects of walls 22, 24 from one another. The proximal portion of the body therefore forms a pair of legs that gives the proximal body greater flexibility to compress inwardly and expand outwardly than at the distal tip. The flexibility of the legs is preferably great enough that the anchor body can be compressed from a frustoconical relaxed shape (as in FIG. 4) to a substantially outwardly cylindrical configuration (as in FIG. 3). The outer diameter of the cylindrical body of FIG. 3 is preferably slightly less than the diameter of a borehole in which the anchor is to be placed. The greatest diameter of the frustoconical expanded anchor body is preferably greater than the diameter of the borehole such that anchor retention in the hole is enhanced.

A retention member is provided on the exterior of the body, in the form of semi-circumferential ridges 42, 44 on the outer face of wall 22 and semi-circumferential ridges 46, 48 on the outer face of wall 24. Each of these ridges is defined by intersecting flat faces 50, 52 (FIGS. 6 and 7) that, in the disclosed embodiment, meet at an angle of about 45 degrees. Face 50 is in a plane perpendicular to the exterior surfaces of walls 22, 24 and the longitudinal axis of body 12. Face 52 slopes inwardly toward the exterior surface of the body such that faces 50, 52 in combination form a sharp retention edge 54 that inhibits extraction of anchor 10 from a borehole after it is placed in the hole and expanded The sharpness of edge 54 can be increased by reducing the included angle between faces 50, 52.

Guide seat 20 at the distal end of internal expansion chamber 18 provides a support surface for an expansion instrument (described below) that allows the instrument to rotate about a fixed axis on the seat without advancing axially. FIGS. 6-7 and 9 show that seat 20 includes a flat, annular face 60 at the distal or deep end of expansion chamber 18. Face 60 circumscribes recess 62 (FIG. 9) that has the shape of a portion of a sphere. Recess 62 is preferably slightly greater than hemispherical in shape, and in the disclosed embodiment has a volume of about two-thirds the volume of a complete sphere.

A suture bore 64 extends completely through distal tip 16 generally perpendicular to the longitudinal axis of elongated body 12. Bore 64 has a diameter great enough to permit a suture 65 to be threaded completely through the bore.

An expansion instrument 70 is shown in FIG. 1 to include an enlarged handle 72 and a tapering shank 74. The exterior surfaces of handle 72 are corrugated to improve effectiveness of manual gripping of the handle 72 by the hand 76 of an operator. A pair of knobs 78, 80 extend in opposing directions from handle 72 and provide retention members about which a thread can be wound. Knobs 78, 80 each include an enlarged head 82, 84 and a reduced diameter neck 86, 88, such that heads 82, 84 prevent dislodgement of thread wound around necks 86, 88. A rubber washer (not shown) is placed around necks 86, 88 in preferred embodiments to enhance retention of suture thread around the necks. The suture may be frictionally locked in place by winding the suture around the neck between the washer and handle 72.

An enlarged view of the distal end of tapering shank 74 is shown in FIGS. 2 and 6–7. The distal end of the shank includes a frustoconical terminal portion 9 that tapers more markedly than the remainder of shank 74. An enlarged button knob 92 is present at the distal end of frustoconical portion 90. Button knob 92 in this embodiment has the shape of a portion of a sphere that is preferably slightly greater than hemispherical. In the disclosed embodiment button knob 92 represents about two-thirds of a sphere. Knob 92 has a shape complementary to and of only a slightly smaller diameter than recess 62. Hence button knob 92 can be snapped into place within recess 62.

The distal end 90 of expansion instrument 70 has an oval cross-section (FIGS. 10–12) that is complementary to the shape of chamber 18. The greatest diameter GD (FIG. 10) of chamber 18 is greater than the greatest diameter gd of end 90. Similarly, the least diameter LD of chamber 18 is greater than the least diameter ld of instrument end 90. Because of the elongated over cross-section and differing diameters of the chamber 18 and instrument end 90, the instrument is capable of rotating about its longitudinal axis through an arc of at least 45–55 degrees before the narrow rounded edges 93, 94 of the instrument end contact arcuate surfaces 26, 28 of chamber 18 respectively. Allowing partial rotation of the instrument before initiating contact with the anchor walls reduces the likelihood that the anchor will merely rotate with the instrument. This delayed wall contact accordingly enhances the effectiveness and certainty of anchor expansion in response to the instrument rotation The frustoconical portion 90 of the tool not only has a lesser diameter than the corresponding chamber 18, but portion 90 also tapers more than chamber 18. As shown in FIG. 7, portion 90 has a greatest diameter that is substantially the same as the expanded diameter of chamber 18. Hence, portion 90 proximally abuts against walls 22, 24, yet tapers away from tapering walls 26, 28 because the degree of taper of portion 90 is greater than the taper of chamber 18. This same relationship holds in FIG. 6 with respect to unexpanded chamber 18, which is substantially cylindrical and does not taper. Portion 90 of the tool, however, does not touch any of the walls of the chamber in the unexpanded condition (FIG. 10), thereby allowing anchor body 12 to pivot about knob 92.

In operation, a cylindrical borehole 95 is initially drilled in a bone 96 (FIGS. 3–5) by a conventional bone drill (not shown). Bone 96 includes an outer or cortical layer 97 and a cancellous inner portion 98. The anchor is placed in the borehole by first inserting the distal end of tapering shank 74 through the open proximal end 14 of body 12 with the lesser diameters of the instrument and chamber aligned as shown in FIG. 10. The tip passes through expansion chamber 18 until button knob 92 comes into contact with the opening of spherical recess 62 in face 60. The width of the opening of spherical recess 62 is less than the greatest diameter of knob 92, hence a slight axially directed force is exerted against shank 74 to force button knob 92 to snap into spherical recess 62. Once button knob 92 has snapped into place, the instrument 70 is free to rotate about the longitudinal axis of the instrument about a point defined by spherical button knob 92. The clearance between the instrument and walls 26, 28 permits the anchor to orient itself relative to the instrument. Anchor 12 is then inserted into bone hole 95 and advanced axially such that the walls of the anchor are deformed inwardly to reduce the effective diameter of the anchor to the diameter of the hole as shown in FIG. 3. The anchor is then advanced to the distal face of the hole 95 and allowed to orient itself relative to the shape of the bone hole by rotating about one or more axes of spherical button knob 92.

After the anchor has been inserted into the hole, the insertion instrument is then rotated through a ninety degree arc from the orientation shown in FIG. 10 to that shown in FIG. 12. As the tool is rotated through about 45–55 degrees, the edges of the oval cross-section that have the smaller radius of curvature impinge against walls 26, 28 and begin to spread walls 22, 24 apart from one another. When the tool has been rotated through a full ninety degrees, the legs are fully separated by an internal chamber diameter of gd, or a distance equal to the greatest diameter of the insertion instrument. Hence, one internal diameter of the chamber increases from LD to gd, while the other internal diameter GD remains constant. The exterior surfaces of walls 22, 24 then frictionally engage the walls of the bore hole, and retention members 42, 44 increase the effective diameter and retention characteristics of more distal portions of the anchor.

The insertion tool is then rotated ninety degrees to an orientation in which the tool does not contact the chamber walls 26, 28. The insertion tool is then withdrawn axially by unwinding the suture 65 from around knobs 78, 80 and withdrawing the tool from the anchor. Slight axial tension may be required to withdraw knob 92 from its corresponding recess, but such withdrawal forces are not great enough to remove the anchor from the borehole. The free ends of suture 65 are then grasped and used to tie tissue, such as a ligament or tendon 99, to the underlying bone 96. Tension may be retained on the suture to maintain tissue 99 against bone 98 by threading the suture through a retainer, as described in U.S. patent application Ser. No. 07/192,813 filed Apr. 20, 1988, which is incorporated herein by reference. Alternatively, the suture 65 is simply tied into a surgical knot 100 after the suture is placed through the tissue 99 with a needle.

An alternative embodiment 112 of the anchor is shown in FIG. 8. Anchor 112 is similar to the anchor of FIGS. 6–7, and like parts are given the same reference numerals plus 100 as those in FIGS. 6–7. This embodiment differs, however, in the shape of the distal tip of the insertion instrument, the shape of the seat, and the configuration of the barbs. The tip of the insertion instrument terminates in a small diameter cylinder 192 that seats in a correspondingly shaped cylindrical recess in seat 120. The cylinder sits in the seat to provide an axis of rotation about which instrument 170 rotates. The cylindrical instead of spherical shape of the instrument tip and seat does not allow the same degree of relative pivoting movement of the anchor relative to the instrument, hence the width of the instrument may be as wide as the unexpanded chamber.

The retention members 42, 44 of FIGS. 6–7 are replaced in FIG. 8 by a plurality of barbs 143 that have arcuate inner and outer faces 145, 147. The radius of curvature of inner face 145 is less than the radius of curvature of outer face 147 such that the barbs are directed upwardly toward the open proximal end of anchor 112. Each barb is wedge-shaped and tapers in the direction of the proximal end of the anchor to form a sharp point. The sharp points are directed at the proximal end of the anchor to inhibit withdrawal of the anchor once it is in place, and especially after the anchor is expanded.

The material used to form the bone anchor may be made of either a bioabsorbable material or a non-bioabsorbable permanent material. Preferred absorbable materials include polyglycolic acid, polylactic acid or trimethylene carbonate copolymers. Preferred nonabsorbable materials include acetal homopolymers or copolymers, polyethylene, polypropylene, polyester and copolymers thereof. The suture material may be any conventional type of suture material, such as Ticron, or Dexon brand sutures which are trademarks of Davis & Geck.

Having illustrated and described the principles of the invention in a preferred embodiment, it should be apparent to those skilled in the art that the invention can be modified in arrangement and detail without departing from such principles. The invention includes all modifications coming within the spirit and scope of the following claims.

The invention claimed is:

1. A bone anchor for securing a suture in a borehole in a bone, comprising:
    an expandable body having a distal tip for insertion distally in a borehole, and an open proximal end, the body defining an expansion chamber that communicates proximally with the open end and defines a seat;
    an expansion slot extending through the body that allows a proximal portion of the body to expand in response to outwardly directed force applied to the body from within the expansion chamber; and
    the expansion chamber having a non-circular cross section with at least one arcuate surface.

2. The bone anchor of claim 1 wherein the expansion chamber comprises two opposing arcuate surfaces.

3. The bone anchor of claim 2 wherein the expansion slot comprises a pair of opposing slots that extend through the proximal end of the anchor and separate the opposing arcuate surfaces.

4. The bone anchor of claim 1 wherein the seat is at the distal end of the expansion chamber and defines a recess having a shape of a cylindrical bore, wherein the bore is of a lesser diameter than the least diameter of the expansion chamber.

5. The bone anchor of claim 1 wherein the seat is at the distal end of the expansion chamber and defines a recess having a shape of at least a portion of a sphere, wherein the sphere is of a lesser diameter than the least diameter of the expansion chamber.

6. A kit for securing a suture in a borehole in a bone, comprising:
    a bone anchor including an expandable body having a distal tip for insertion distally in a borehole, and an open proximal end, the body defining an expansion chamber that communicates proximally with the open end and defines a seat, the body further defining a means for carrying a suture therein;
    an expansion slot extending through the body that allows a proximal portion of the body to expand in response to outwardly directed force applied to the body from within the expansion chamber; and
    an expansion instrument that is insertable through the proximal end into the expansion chamber.

7. The bone anchor of claim 6 further comprising a retention member on the exterior of the body that inhibits extraction of the anchor from the borehole after the body has been expanded.

8. The bone anchor of claim 7 further comprising a suture receiving opening in the anchor.

9. The bone anchor of claim 7 wherein the body has a frustoconical cross-section along at least a part of its length, and tapers from its proximal end to distal tip.

10. The bone anchor of claim 6 wherein the expansion instrument comprises a rod having an oblong cross-section portion for insertion into the expansion chamber.

11. The bone anchor of claim 6 wherein the size and shape of the expansion instrument and expansion chamber allow the instrument to rotate on the seat without advancing axially, from a first position in which the instrument does not apply the outwardly directed force to the body, to a second position in which the instrument applies the outwardly directed force to the body to expand the body.

12. The bone anchor of claim 11 wherein the size and shape of the instrument and expansion chamber allow the instrument to rotate through more than about forty-five degrees from the first to second position.

13. The bone anchor of claim 12 wherein the expansion chamber is an oblong ovoid in cross-section, and the expansion tool comprises a portion that has a corresponding shape with a lesser greatest diameter.

14. The bone anchor of claim 11 wherein the suture receiving opening extends through the tip.

15. The bone anchor of claim 6 further comprising a guide member at a distal end of the expansion instrument having a shape complementary to the shape of the seat, and the expansion chamber of the bone anchor comprises a corresponding recess at a distal end of the chamber in which the guide member seats and is free to rotate.

16. The bone anchor of claim 6 wherein the expandable body tapers to a solid distal tip.

17. A kit for securing a suture in a bone borehole, the anchor comprising:
    a bone anchor including an expandable anchor body having a solid distal tip and an open proximal end, the body tapering in the direction of the distal tip and defining an expansion chamber that communicates proximally with the open end and distally with a guide seat, the expansion chamber having an oblong ovoid cross-section with walls that form a pair of opposing arcuate guide surfaces;

a pair of opposing expansion slots extending through the walls and the proximal end, and separating the opposing arcuate guide surfaces along a portion of the body such that a proximal portion of the body is expandable;

a retention member on the exterior of the body that inhibits extraction of the anchor from the borehole after the anchor has been expanded;

an elongated expansion instrument that is insertable into the expansion chamber, the instrument having an oblong ovoid shape with a greater and lesser diameter that are respectively less than a greater and lesser diameter of the chamber; and a rotary guide member on the instrument that cooperates with the guide seat of the chamber to seat the instrument in the chamber and provide an axis of rotation of the instrument relative to the body.

18. The bone anchor of claim 17 wherein the guide seat and guide member are spherical.

19. The bone anchor of claim 17 wherein the guide seat and guide member are cylindrical.

20. A method of anchoring a suture to a bone, comprising:

drilling a borehole in a bone;

inserting a bone anchor, carrying a portion of a suture, into the borehole with the distal tip positioned distally in the hole; and placing an expansion instrument into the expansion chamber through the proximal end of the anchor and expanding the proximal end of the bone anchor by rotating the instrument.

21. The method of claim 20 wherein the expansion chamber has at least one arcuate surface, and the expansion instrument comprises a rod with a member that engages the arcuate surface to exert progressive outward force against the surface as the rod rotates, and the step of expanding the bone anchor comprises rotating the rod.

22. The method of claim 20 further comprising selectively securing the anchor to the instrument before inserting the anchor in the borehole.

23. The method of claim 22 wherein the step of selectively securing the anchor comprises providing a suture thread through the anchor, and attaching the thread to a retainer on the instrument.

24. The method of claim 20 further including placing a suture through the bone anchor prior to inserting the bone anchor into the bore hole.

* * * * *